United States Patent [19]
Dasgupta

[11] Patent Number: 5,814,199
[45] Date of Patent: Sep. 29, 1998

[54] FORMING THIN FILM INTERFACED SAMPLES FOR ANALYSIS WITH CAPILLARY SEPARATION SYSTEMS

[75] Inventor: Purnendu K. Dasgupta, Lubbock, Tex.

[73] Assignee: Texas Tech University, Lubbock, Tex.

[21] Appl. No.: 717,550

[22] Filed: Sep. 20, 1996

Related U.S. Application Data

[60] Provisional application No. 60/004,127 Sep. 21, 1995.
[51] Int. Cl.$^6$ .......................... G01N 27/26; G01N 27/447
[52] U.S. Cl. ............................................ 204/453; 204/604
[58] Field of Search .................................. 204/451, 452, 204/453, 454, 455, 601, 602, 603, 604, 605

[56] References Cited

U.S. PATENT DOCUMENTS

| | | | |
|---|---|---|---|
| 5,122,248 | 6/1992 | Karger et al. | 204/455 X |
| 5,358,612 | 10/1994 | Dasgupta et al. | 204/452 |

OTHER PUBLICATIONS

Donald J. Rose, Jr. and James W. Jorgenson, "Characterization and Automation of Sample Introduction Methods for Capillary Zone Electrophoresis" Analytical Chemistry, vol. 60, No. 7 (1 Apr. 1986) 642–648.

Susumu Honda et al, "Evaluation of an Automatic Siphonic Sampler for Capillary Zone Electrophoresis" Journal of Chromotography 404 (1987 No month available)313–320.

Cardoso, A.A. and P.K. Dasgupta, "Analytic Chemistry in a Liquid Film/Droplet," Analytical Chemistry, 67(15):2562–2566 (Aug. 1, 1995).

Liu, S. and Dasgupta, P.K., "Liquid Droplet. A Renewable Gas Sampling Interface," Analytical Chemistry, 67(13):2042–2049 (Jul. 1, 1995).

Dasgupta, P.K. and L. Bao, "Suppressed Conductometric Capillary Electrophoresis Separation System," Analytical Chemistry, 65(8):1003–1011 (Apr. 15, 1993).

Simon, P.K. and P.K. Dasgupta, "Wet Effluent Denuder Coupled Liquid/Ion chromotography Systems: Annular and Parallel Plate Denuders," Analytical Chemistry, 65(9):1134–1139 (May 1, 1993).

Bao, L. and P.K. Dasgupta, "Membrane Interfaces for Sample Introduction in Capillary Zone Electrophoresis," Analytical Chemistry, 64(9):991–996 (May 1, 1992).

Hinds, W.C., Aerosol Technology: Properties, Behavior, and Measurement of Airborne Particles, John Wiley & Sons: New York (1992), pp. 160–163.

Primary Examiner—Robert J. Warden
Assistant Examiner—John S. Starsiak, Jr.
Attorney, Agent, or Firm—Flehr Hohbach Test Abritton & Herbert LLP

[57] ABSTRACT

Direct measurement of soluble ionogenic atmospheric gases is implemented using a suppressed conductometric capillary electrophoresis separation system. A small circular wire loop is incorporated adjacent sampling end of a fused silica capillary, in the same plane as the capillary. Dipping the loop into a solution and then withdrawing forms a liquid film that is in fluid communication with the capillary and acts as a microreservoir. Elevating the film relative to the destination side injects part or all of the film contents into the capillary. This mechanism may be used to perform gas sampling in automated fashion with slightly modified commercial CE instrumentation. The film-bearing loop is lowered into a sample chamber and air is sampled for a preset time period at a preselected flow rate. Lifting the capillary introduces an aliquot from the film for analysis. The capillary is then dipped into a running electrolyte source vial and electrophoresis is commenced. The system may be used with other than suppressed conductivity detection units and/or non-aqueous electrolytes.

16 Claims, 11 Drawing Sheets

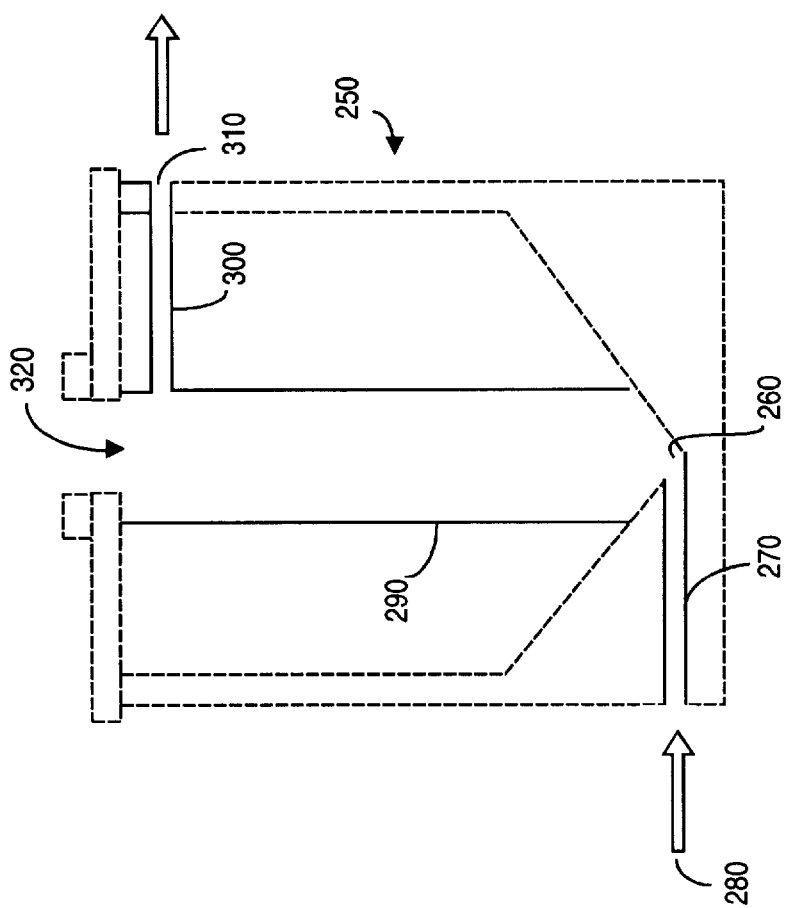

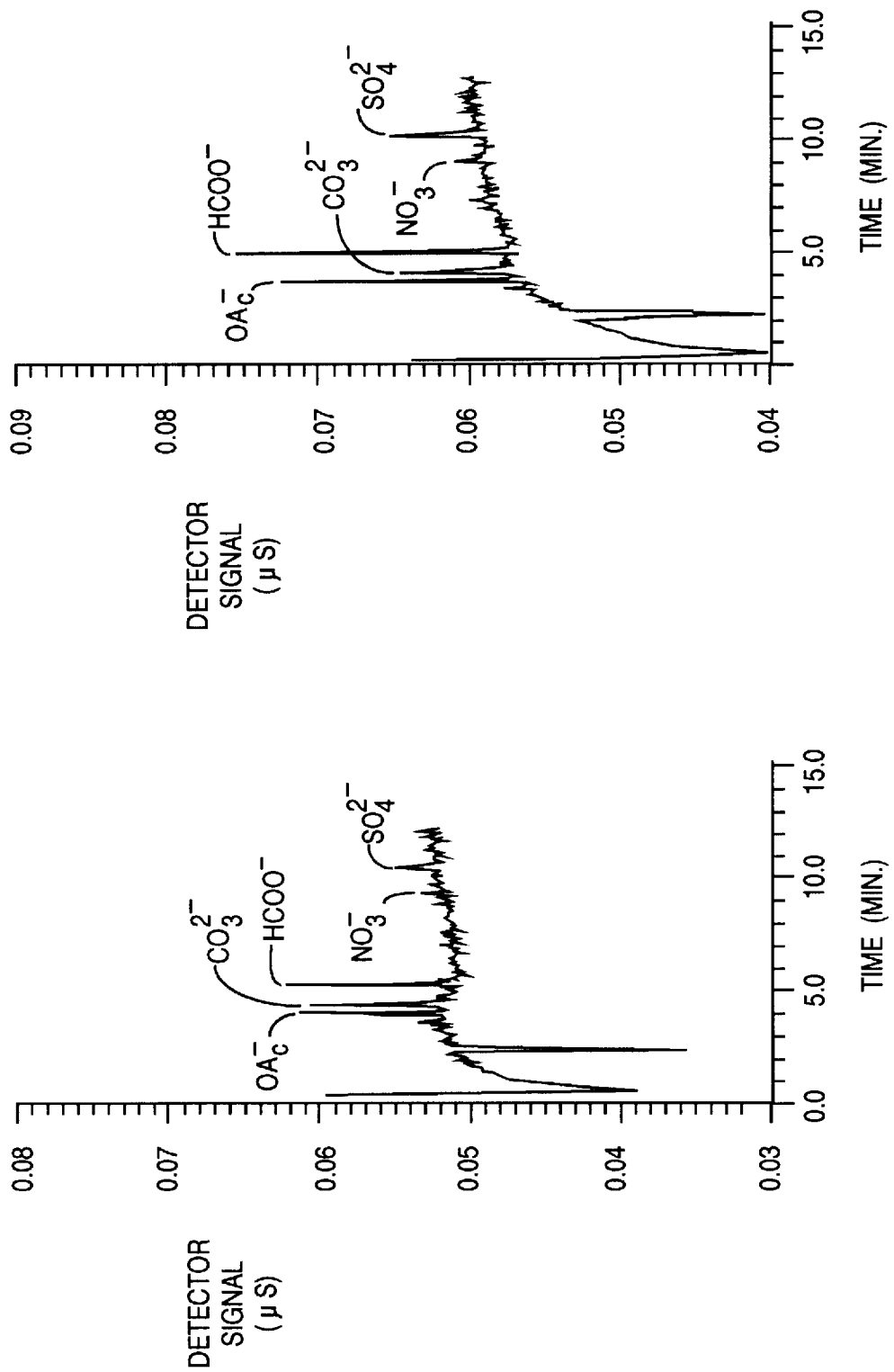

FORMING THIN FILM INTERFACED SAMPLES FOR ANALYSIS WITH CAPILLARY SEPARATION SYSTEMS

RELATIONSHIP TO PREVIOUSLY FILED APPLICATIONS

Priority is claimed from U.S. provisional application number 60/004,127, filed Sep. 21, 1995.

FIELD OF THE INVENTION

This invention relates generally to measurement of gases in capillary electrophoresis separation systems, and more particularly to providing such systems with a renewable, microscale gas sampling interface that inhibits approach of particulate matter into the same.

BACKGROUND OF THE INVENTION

Capillary electrophoresis and associated capillary scale technologies have rapidly and profoundly changed how analytic separation and measurements are carried out. These technologies have provided very important analytic techniques for separation and quantitation of large biomolecules. Although such techniques have also proved useful in separating and detecting small ions, ion chromatography has been a more dominant technique. The more successful ion chromatography detection techniques have recently been found to be applicable to capillary electrophoresis. The result has been so-called suppressed conductometric capillary electrophoresis separation systems ("SuCCESS"). SUCCESS technology can produce low $\mu$g/L limits of detection for a variety of small ions in a robust manner without special efforts towards pre-concentration.

As described by P. K. Dasgupta and L. Bao in *Anal. Chem* 1993, 65: 1003–1011 and shown in FIG. 1, a SuCCESS configuration 10 includes a capillary 20 whose distal end 30 initially is in fluid communication with a solution 40 containing analyte samples A, and typically also containing other substances X, including perhaps particulate matter. Solution 40 is retained in a source vessel 50 and is electrically coupled by an electrode 55 to a power source 60 that is at a high voltage potential V1, typically many kilovolts. Various regions, shown in FIG. 1 as black rectangles, may serve as grounding nodes to which the ground terminal of power supply 60 may be coupled. Coupling power supply 60 to capillary 20 results a left-to-right direction migration of analyte A within the capillary, as indicated by the rightward-pointing arrows.

Such migration can commence within seconds of energizing power supply 60. Power supply 60 may then be turned-off, after which tip 30 of capillary 20 is relocated into a second vessel 70 containing running electrolyte 80. Power supply 60 is coupled to solution 80 via an electrode 55, which may be identical to (or indeed the same as) electrode 55 described in conjunction with vessel 50. Power source 60 may then be re-energized, which continues the downstream migration of the sample analyte, and unfortunately other matter within solution 40 as well.

The downstream end 90 of capillary 20 is coupled to the input of a vial 100 containing a regenerate 110. A membrane suppressor 120 is coupled between the input port and output port of vial 100. Suppressor 120 preferably is a cation exchanger for anion determinations, and is an anion exchanger for cation determinations. The output port of vial 100 is coupled to the input of a conductivity detection cell 130, downstream from which is coupled a capillary 140. The distal end of capillary 140 is in fluid communication with electrolyte 150 contained in a terminating electrolyte reservoir 150. Preferably electrolyte 150 is the same as running electrolyte 80.

Ion chromatography has proven especially beneficial in the analysis of atmospheric samples, although capillary electrophoresis-based analyses of atmospheric filter samples have also been attempted. Unfortunately analytic technology and the sample collection strategies have not been necessarily optimally matched. For example, although $\mu$L scale samples are adequate to provide nL scale injections used in capillary electrophoresis, atmospheric filter samples typically obligatorily produce extraction volumes in the order of several mL.

It has been recognized that, relative to particles, atmospheric gases may be sampled more directly and in a microscale. For example, Bao, L. and Dasgupta, P. K. in *Anal. Chem.* 1992, 64: 991–996 describe a technique in which a microscale membrane based diffusion scrubber constituted an integral part of the separation capillary. A small segment of a porous hydrophobic membrane capillary was used to connect a fused silica separation capillary to a small length of an "entrance" fused silica separation capillary. A jacket was built around the membrane and air sampled around it, whence analyte gases of interest diffused through the pores. These gases were trapped by the internal electrolyte, and electrophoresis was then commenced. Optical detection, direct or indirect, produced respectable limits of detection even though such detection methods are less sensitive than suppressed conductometry methods. Unfortunately this Bao-Dasgupta technique had several shortcomings. The membrane was too fragile, and soiling tended to change the sample transfer function over prolonged use. Further, facile evaporation of the internal liquid through the membrane pores necessitated a "dry flush", even during an analysis.

In short, there is a need for a more direct and efficient method and apparatus for sampling a gas sample. Preferably such method and apparatus should function on a microscale, and be substantially independent of measurement difficulties stemming from membrane fouling. Further, the membrane interface should be indefinitely renewable.

The present invention describes a sampling method and apparatus for use in carrying out such measurements.

SUMMARY OF THE PRESENT INVENTION

The present invention provides a gas sampling interface comprising a liquid or gaseous film for use in an electrophoresis separation system. The resultant interface is indefinitely renewable, is employed in a microscale, and advantageously inhibits the approach of particles due to evaporative flux from the film.

A wire loop of a few mm diameter is formed at the tip of the sampling distal end of a preferably fused silica separation capillary. This loop, which defines a plane parallel to a plane of the distal region of the capillary, is immersed in the sample analyte, and withdrawn, whereupon a film forms across the loop. The liquid or gaseous film across the loop is in fluid communication with the capillary and acts as a microreservoir.

The film-bearing loop may be automatically lowered into a sample chamber and air is sampled for a preset time period at a preselected flow rate. Lifting the capillary introduces an aliquot from the film for analysis. The capillary is then dipped into a source of running electrolyte, whereupon capillary electrophoretic separation is commenced by application of high voltage across the capillary. Downstream, a preferably suppressed conductivity detector analyzes the sample constituents.

Other features and advantages of the invention will appear from the following description in which the preferred embodiments have been set forth in detail, in conjunction with the accompanying drawings.

BRIEF DESCRIPTION OF THE DRAWINGS

FIG. 3C depicts a chamber-volume reducing member for a source vial, with which the present invention may be practiced;

FIGS. 8A and 8B depict detector signal versus time for different sampling times, according to the present invention;

DETAILED DESCRIPTION OF THE PREFERRED EMBODIMENT

Figure 1:
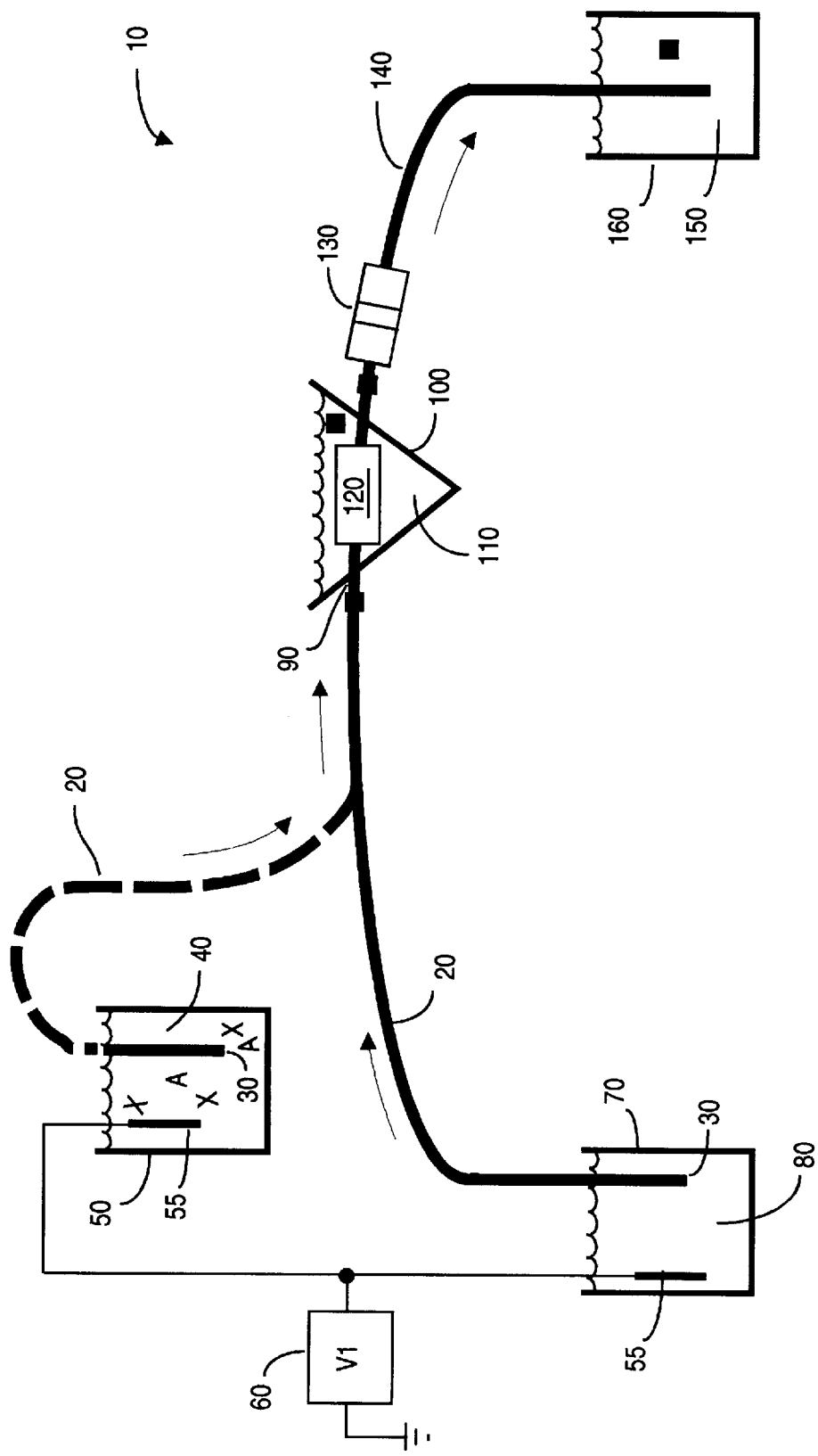
FIG. 1 depicts a so-called SuCCESS system, according to the prior art.
Figure 2:
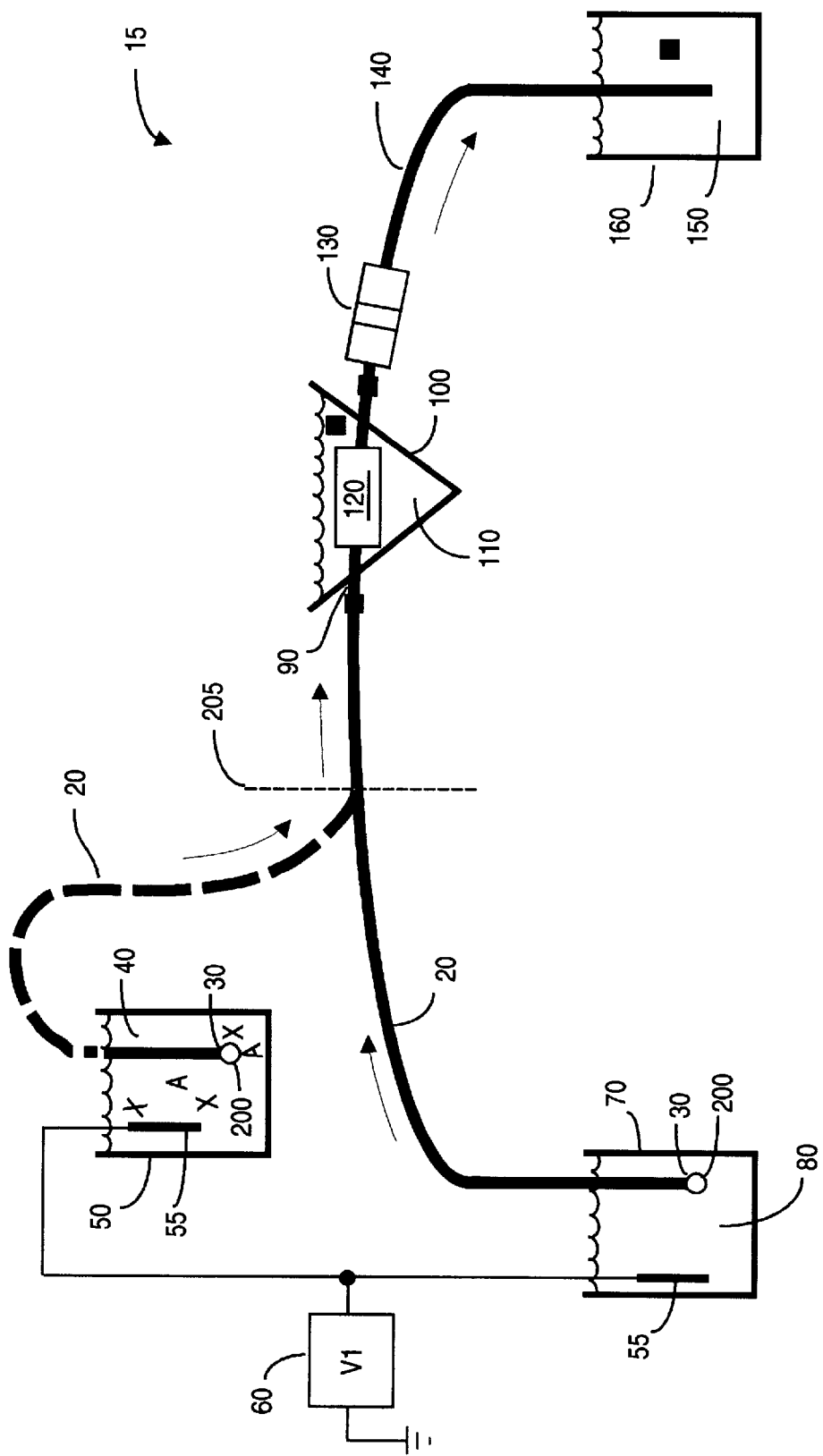
FIG. 2 depicts a capillary electrophoresis separation system provided with a film microreservoir, according to the present invention.

FIG. 2 depicts a capillary electrophoresis separation system 15, in which the distal end 30 of a preferably fused silica separation capillary 20 is provided with a small wire loop 200. But for loop 200, the remainder of system 15 may (but need not be) the same as that shown in prior art FIG. 1. However, it will be appreciated that system components downstream from vertical line 205 are directed to a specific manner of analyte detection (here suppressed conductometric measurement). In practice, other downstream measurement and detection techniques may be used. When loop 200 is dipped or submerged within solution 40 in vial 50, and then withdrawn, a film of solution forms across the loop. This film is in fluid communication with the capillary, and functions as a microreservoir.

The present invention primarily is directed to the sampling loop 200 used at the front end or input side of a capillary electrophoresis separation system. Thus, in FIG. 2, the specifics of the detection and measurement configuration downstream from vertical line 205 are relatively unimportant. As shown, however, suppressed capillary electrophoresis was used in the preferred embodiment, in which vial 100 contained 5 mM $H_2SO_4$ regenerate 110. Suppressor 120 was a Nafion membrane suppressor unit, and detection cell 130 preferably was a bifilar wire conductance cell used with a Dionex Corporation (Sunnyvale, Calif.) model CDM-I conductivity detector.

High voltage power supply 60 and the sample/capillary transport capabilities (indicated in FIG. 2 by the phantom-line drawn and solid-line drawn capillary 20 positions) were provided by a Dionex Corporation model CES-1, which permitted complete automation of the SuCCESS-based gas sampling and analysis system shown. As such, the sampling end of capillary 20 (e.g., the portion including loop 200) and the high voltage electrode 55 were affixed to a common head that could make limited but programmable movements in three dimensions.

Figure 3B:
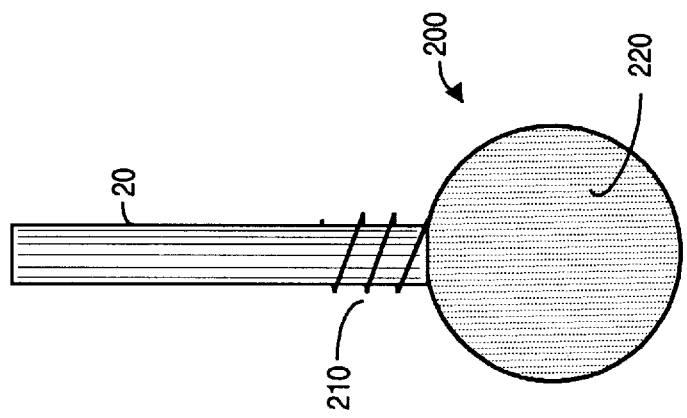
FIG. 3B is a photomicrograph showing a liquid film formed on a sampling loop, according to the present invention.
Figure 3A:
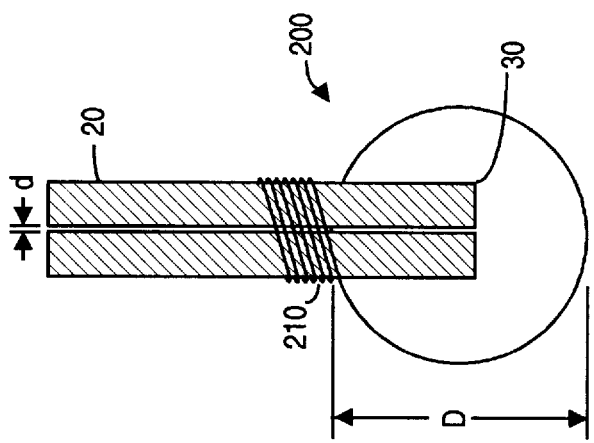
FIG. 3A depicts a wire loop attached to the sampling end of a capillary so as to form a film microreservoir, according to the present invention.

As best shown in FIG. 3A, loop 200 is a closed perimeter circular-shaped member preferably fabricated from a length of wire 210 that is wrapped adjacent end 30 of capillary 20 before forming the loop. In the preferred embodiment, the loop is circular shaped, having a diameter D of about 2 mm, and is formed from platinum wire having outside diameter of about 100 $\mu$m. Capillary 20 was a fused silica separation capillary unit whose inner diameter d was about 75 $\mu$m, and whose length was about 45 cm. As shown in FIG. 3A, the plane of loop 200 is parallel to the longitudinal axis of capillary 20, in the same sense that the hitting surface of a ping-pong paddle is parallel to the longitudinal axis of the handle of the paddle.

FIG. 3B is a photomicrograph showing a liquid film 220, e.g., of sample solution 40, formed on sampling loop 200, so as to form a microreservoir. After immersing loop 200 solution 40, the loop was withdrawn, at which time the photomicrograph was made. When held up, the liquid in the loop had the shape of a biconvex lens, e.g., bulging in the middle to just beyond the dimensions of the capillary. Based on microscopic observations, the radius of curvature was estimated to be about 4 mm.

The volume of a spherical cap, $V_{cap}$, of radius of curvature r and height h is given by:

$$V_{cap} = \pi h^2 (3r-h)/3 \qquad (1)$$

while the volume occupied by the capillary, $V_{capillary}$, itself is:

$$V_{capillary} = \pi r_c^2 L \qquad (2)$$

where the outer radius of the capillary, $r_c$ is 0.18 mm and its length within the film, L, is 1.1 mm. The overall liquid volume in the film, $V_{film}$ is then estimated to be:

$$V_{film} = 2V_{cap} - V_{capillary} \qquad (3)$$

The volume of the loop is determined by measuring the mass of water lost from a small tared water filled vial upon the insertion and withdrawal of an initially empty wire loop. The measured value was 880 nL±70 nL (n=12), which is in excellent agreement with the value of calculated from equation (3) 3 where h is 0.2 mm.

Using system 15, a typical "normal" sequence is to move the sampling end 30 of the running electrolyte-filled fused silica separation capillary 20 to a sample vial 250 (shown in FIG. 3C), located in a programmable rotatable turret. In the model CES-1, the sampling head makes a gasket-based seal with sample-containing vessel or vial 50. The sample may be introduced either (a) by electromigration, (b) by applying a pneumatic pressure pulse through a port in the head, or (c)

by grasping vial 50, and lifting the head and vial 50 so as to introduce the sample by gravity.

The head is then returned to a "source vial" chamber 250 (see FIG. 3C) where the head again makes a seal and dips into the running electrolyte. Electrophoresis is then begun by activating or reactivating high voltage power supply 60. In the preferred embodiment, the source vial contains connections that allow refilling with fresh running electrolyte or other wash liquids, and pneumatic pressurization for flushing capillary 20. In one embodiment, the source vial was used as the gas sampling chamber.

FIG. 3C depicts minor changes made to the source vial chamber 250 of a Dionex Corporation model CES-1 unit to better accommodate the present invention. As modified, the distal dip of capillary 20 could be filled with running electrolyte 80 or other wash liquids, and pneumatic pressurization could be provided for flushing the capillary.

With reference to FIG. 3C, sample vial 250 includes a bottom port 260 that was enlarged and connected to a polytetrafluoroethylene ("PTFE") tube 270 through which sample gas 280 (shown by incoming arrow) entered the preferably polyvinyledene fluoride source vial. The source vial per se had an inner diameter of 41.5 mm, which was reduced by installation of a 9.5 mm inner diameter polyethylene tube 290, thus reducing the effective sampling chamber volume. Approximately 7 mm from the top, a flexible polyvinyl chloride tube 300 connected tube 290 to a gas outlet side port 310 drilled on the side of the source vial as shown. (The outlet gas is shown by the exiting arrow.) Side port 310 was connected to a sampling pump or other apparatus. An opening 320 in the top of source vial 250 admitted the sampling tip of capillary 20.

For the experiments described herein, the rotatable sample turret contained alternating vials of the liquid used for the sampling film (0.15% $H_2O_2$, 44 mM) and the running electrolyte used for the capillary electrophoresis run (2 mM $Na_2B_4O_7$). A standard operating procedure consisted of (a) dipping the sampling head into a vial holding $Na_2B_4O_7$, pressurizing to flush the capillary with the running electrolyte, lifting the sampling head and dipping it into the film making liquid, withdrawing it and introducing it into the gas sampling chamber (formerly termed the source vial).

Note that there is no significant hydrostatic difference between the film contents and the detector end of the capillary during sampling. Air was sampled immediately after the head sealed itself on the sampling chamber. Following the sampling period, the head was lifted to a height of 10 cm and maintained in that position for a fixed period of time to introduce an aliquot of the film contents into the capillary. Then the head was returned to a fresh $Na_2B_4O_7$ vial and +15 kV high voltage potential was applied to begin the electrophoretic run.

Figure 4:
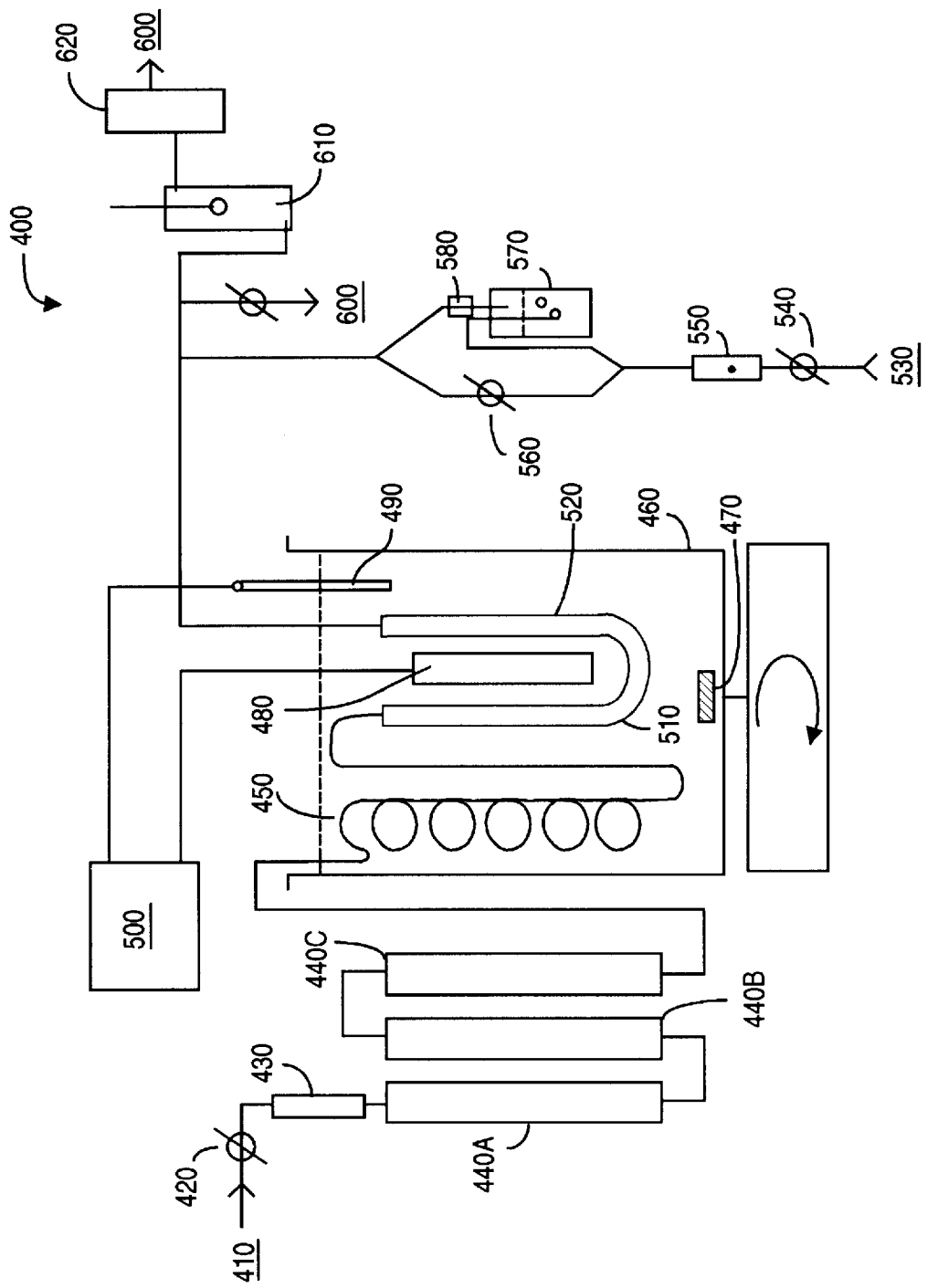
FIG. 4 is a schematic of a $SO_2$ generator, with which the present invention may be practiced.

FIG. 4 depicts the calibrant gas generation system 400 used in the preferred embodiment. House air 410 was metered through a needle valve 420 and flow meter 430 at a typical flow rate of 70 $cm_3$/min) through sequential columns 440A, 440B, 440C containing activated charcoal, silica gel and soda-lime, respectively. The air then entered a thermal equilibration coil 450 in a water bath 460 stirred by a stir bar mechanism 470. That bath was maintained at about 30° C. by a 100 W heater 480 and a Thomas Scientific mercury contact thermoregulator 490, under control of relay 500.

The thermally equilibrated air was admitted into a glass permeation chamber 510 containing a permeation wafer 520 that emitted $SO_2$ at a gravimetrically calibrated rate of 0.27 ng/min. The $SO_2$ bearing air was diluted with dilution air 530 (whose flow rate was typically 50 $cm_3$/min. to 1500 $cm_3$/min). Dilution air 530 was metered through a needle valve 540 and flow meter 550.

As shown in FIG. 4, dilution air downstream from flow meter 550 was split in two streams. One stream proceeded through a needle valve 560. The other stream proceeded through a water filled bubbler 570 and a glass wool trap 580, to remove any entrained water droplets before being recombined again as the dilution stream. By adjusting needle value 560, the degree of humidification of the dilution air stream could be controlled.

Part of the diluted $SO_2$ stream was vented under control of a needle valve 590 to waste 600. The remainder of the stream proceeded through gas sampling chamber 610. In some experiments, needle valve 590 was fully open and the desired sampling flow rate was attained by unit 620, which was a sampling pump equipped with its own flow control valve. In other experiments, unit 620 was a primary standard digital bubble meter (preferably from Gilibrator, Gilian Instrument Corp., of West Caldwell, N.J.) that was placed at the gas sampling chamber output, with sampling flow adjusted by controlling the venting rate with needle valve 590. In other experiments, unit 620 was a capacitance type relative humidity probe that measured relative humidity of the sample air.

The air flow rates referred to herein are true volume flow rates at the ambient conditions for the experiments, 680 mm Hg and 22° C. These rates need to be multiplied by a factor of 0.828 for conversion into values at standard temperature and pressure. Unless otherwise stated, gas sampling was conducted at 100 $cm_3$/min for 1 min and the hydrostatic sample introduction period was 20 s.

$SO_2$ was selected as a test gas, not only because of its importance as an atmospheric pollutant but also because the performance of system 15 with $SO_2$ is likely to represent lower limits of detections. Positive polarity was used in the SuCCESS-type configuration, and ions electromigrate opposite to the electroosmotic flow. Weaker acid gases such as HCOOH have lower mobility anions that elute rapidly, resulting in more easily detectable peaks relative to sulfate resulting from $SO_2$. Other common acid gases such as HONO or HCl have a larger diffusion coefficient than $SO_2$. This should result in more efficient collection by the film 220 within loop 200, assuming that the film composition is chosen to be an effective sink for the gas.

Experiments with wet effluent diffusion denuders have shown that $H_2O_2$ is an efficient absorbing liquid for capturing $SO_2$, wherein the collected gas is oxidized to sulfate. (See Simon, P. K.; Dasgupta, P. K. Anal. Chem. 1993, 65, 1134–1139.) However, initial experiments indicated that 1 mM or lower $H_2O_2$ concentrations used with wet effluent diffusion denuders were quite insufficient for the present case. The observed signal for 19 ppb to 100 ppb $SO_2$ increased with increasing $H_2O2Wxx$ concentrations in the 1–35 mM range. The solution contained in the film was essentially stagnant, and only the reagent present on the surface was effective for capturing the analyte.

In wet effluent diffusion denuders, absorber flows down a surface and convective/frictional/turbulent forces can bring new reagent to the surface. However, in the present invention, diffusion is the only motive force to replenish surface reagent, and diffusion is a slow process in the liquid phase. Consequently the concentration of the absorber reagent used should be higher. However, reagent blank also increases with increasing concentration, which is detrimental to any type of trace analysis.

Experiments were conducted using two different $H_2O_2$ stock reagents from two different manufacturers: a 3% concentration, and a 30% concentration. The presence of sulfate as an impurity was particularly noticeable in the 3% $H_2O_2$ stock solution used in experiments. After appropriate dilution, impurity levels were significantly lower in 30% $H_2O_2$ solutions.

The minimum concentration of $H_2O_2$ necessary to function as a fully effective sink also depends on the concentration of $SO_2$ to be sampled and the sampling duration. Based upon experimental experience relating to ambient levels of $SO_2$, a maximum anticipated $SO_2$ concentration of 50 ppb and a sampling duration of 60 seconds seemed appropriate. A concentration of 45 mM (~0.15%) $H_2O_2$ was found adequate for dealing with these maximum anticipated levels, although the $H_2O_2$ concentration should be increased if higher levels must be determined. If levels of detection must also be maintained at previous levels, it may be necessary to clean the $H_2O_2$ used, to remove residual sulfate.

Water by itself may serve as a suitable collection medium for some gases, but water is not ideal for collecting $SO_2$. Aside from lower sensitivity relative to the use of $H_2O_2$, in the absence of reactive uptake, the film becomes quickly surface saturated. Strong nonlinearity is observed as a function of either sampling time or sample concentration.

An alkaline medium, such as the borate solution used as the electrolyte, can also serve as an effective sink for an acidic analyte gas such as $SO_2$. However, in such case the acidic gas is analyzed as sulfite and detected as a monoprotic acid after suppression with consequent loss of sensitivity. Further, the sample can be partially oxidized to sulfate during electrophoresis. This results in a broad peak that appears at a retention time intermediate to that of sulfite and sulfate, which leads to difficulties in quantitation. An alkaline absorbent also absorbs $CO_2$ efficiently, which results in a large carbonate peak. Another advantage in using $H_2O_2$ as the collecting medium, relative to using running electrolyte for the purpose, is electrostacking. This can effectively occur with a low ionic strength low conductance medium, but not with an equal or higher conductance medium. (See, for example, Chien, R -L.; Burgi, D. S. Anal. Chem. 1992, 64, 489A–496A.) If an electrolyte is used for collection, some concentration is bound to occur during sampling due to evaporative losses of the solvent.

Figure 5A:
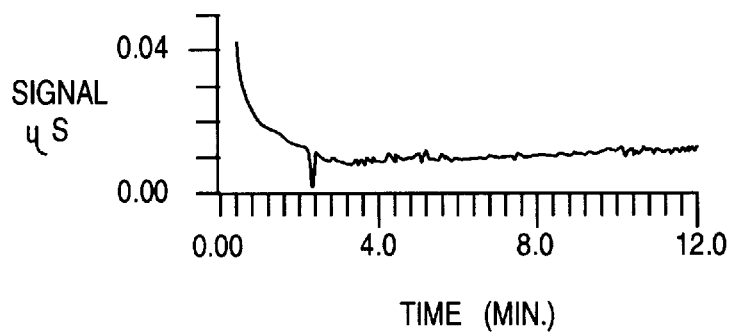
FIG. 5A is an electropherogram obtained using a film water blank sample, according to the present invention.
Figure 5B:
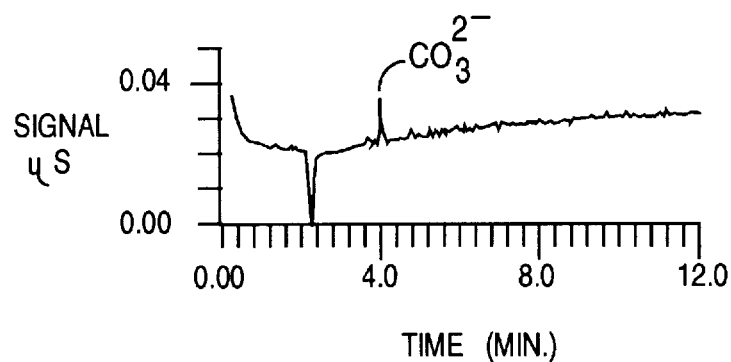
FIG. 5B is an electropherogram obtained using a film $H_2O_2$ blank sample, according to the present invention.
Figure 5C:
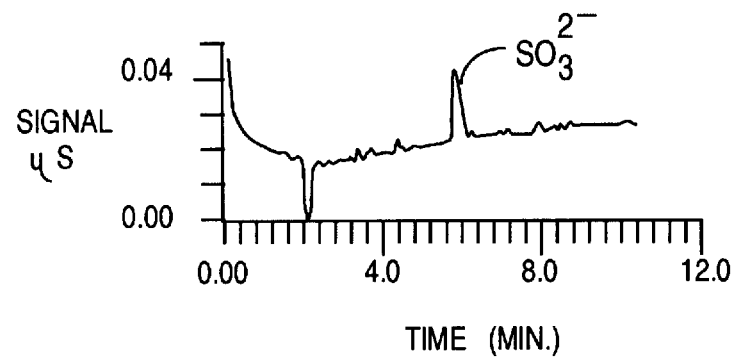
FIGS. 5C–5E are electropherograms obtained using film $SO_2$ blank samples with different absorber solutions, according to the present invention.
Figure 5D:
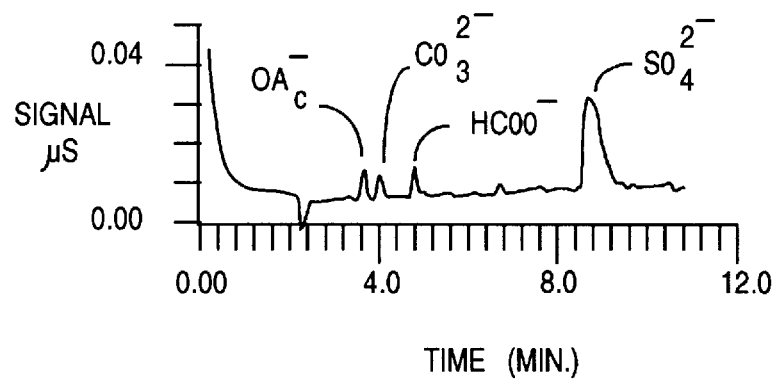
Figure 5E:
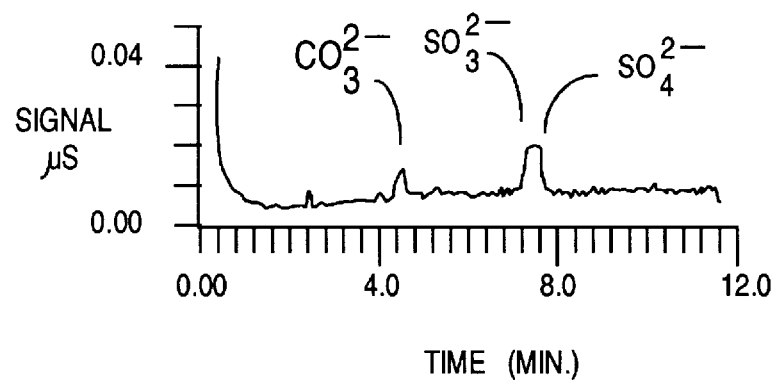

FIGS. 5A–5C depict the above effects, showing electropherograms obtaining by introducing a sample from the film, with detection signal ($\mu S$) plotted on the vertical axis versus time (minutes) on the horizontal axis. FIG. 5A is an electropherogram of pure water introduced from the film. In the electropherogram of FIG. 5B, 45 mM $H_2O_2$ was introduced from the film, without sampling $SO_2$. FIG. 5C is an electropherogram for 20 ppb $SO_2$ sampled with the $H_2O$ as an absorber. FIG. 5D represents 20 ppb $SO_2$ sampled with $H_2O_2$ as absorber. Finally, the electropherogram of FIG. 5E represents 20 ppb $SO_2$ sampled with 2 mM $Na_2B_4O_7$ as absorber.

The formation of loop 200 has been described above with respect to FIGS. 3A and 3B. When the loop is lifted with respect to the destination vial, hydrostatic introduction of the sample occurs, although several differences with respect to conventional hydrostatic injection should be noted. Given the same hydrostatic head, the rate of sample introduction will be different for the present invention due to surface tension.

In testing, the rate of sample introduction was evaluated by measuring peak area resulting from introducing a 0.1% N,N-dimethylformamide solution for different periods of time and optical detection of the resulting signal. For a sample introduction period of up to 90 s, the signal was linearly related to the introduction time. The uncertainty of linear slope was <3%, the intercept was indistinguishable from zero at the 95% confidence level, linear r=0.9933, and a total of 17 measurements at five separate introduction periods were made. At the end of 90 s, less than 25% of the original film volume has been introduced.

The rate of liquid introduction becomes slower at longer introduction times and finally the film breaks. As the liquid at the tip of the capillary is depleted, sample introduction stops altogether. Unless an excessive hydrostatic head is applied, air actually never enters the hydrophilic capillary. A small amount of the original film contents are left on the wire loop and are never introduced. By constructing the loop differently, e.g., by placing the capillary on the periphery, rather than at the center of the loop, it would be possible to inject virtually all of the loop contents into the capillary, especially for small loops. Nevertheless, without extraordinary measures towards electrostacking, this is likely to be too large a sample volume to be used in its entirety.

Since total amount of sample introduced by conventional gravity injection is readily calculated using known methods (e.g., Grossman, P. D., Colburn, J. C. "Capillary Electrophoresis: Theory and Practice", Academic Press, San Diego, Calif. 1992), the sample amount introduced from a film can be estimated by comparison of peak areas. The volume of the sample injected from the film during a 20 s period with a 10 cm hydrostatic head can be ascertained to be 37 nL±3 nL, about 90% of the value when the sample is introduced from a vial. Reproducibility of sample injection from the film by such hydrostatic means was examined by making the film from a standard sample solution containing $ClO_3^-$ and $SO_4^{2-}$, and performing a 40 s, 10 cm introduction. Relative standard deviations ("RSD") for the two analyses were found to be 1.8%–2.2%. These values were no worse than the RSD of 1.8%–3.9% observed in the described system with conventional hydrostatic injection of liquid samples.

An aliquot from the film can also be introduced by bringing the head down on an empty vial and using a pneumatic pulse. The RSD for such approach was 0.4%–4.8%, using a 2 s, 2.5 psi pressure pulse, which introduces an amount comparable to that from a 20 s 10 cm hydrostatic introduction). This 0.4–4.8% RSD was essentially the same as that observed for pressure injections made from vials.

Homogeneity of the film at the time of sample injection was investigated.. Applicant had helped previously established the nature of analyte distribution for a pendant drop at the tip of a capillary for $NH_3$ analyte gas diffusing into an acidic drop in a capillary format sequential injection analysis system. Analyte concentration is much higher at the surface and is very low at the tip of the capillary. Indeed, the first aliquot withdrawn into the capillary in such case contains almost no analyte.

However, using the present invention a more favorable situation exists. The film is much thinner than the drop, and mixing-induced by surface circulation should be much more efficient. Such mixing-induced effects appear to be brought about by the frictional drag of the moving gas.

However, one can calculate the characteristic mixing time within the film, even in the absence of such mixing. The calculation can be approximated to be $t^2/D$, where t is half the maximum thickness of the film and D is the diffusion coefficient of the analyte. Because it is not expected that a large fraction of the gas is removed, one can assume that a uniform surface concentration. Thus, there is no significant dependence from the bottom to the top of the film. Assuming average film thickness of about 250 $\mu$m, the diffusion coefficient D for $SO_4^{2-}$ can be readily calculated from its equivalent conductance to be $2.45 \times 10^{-5}$ cm$^2$/s, and the radial mixing time is therefore only about 6.3 s.

Post-sampling transport of the capillary to the sample introduction position requires 12–13 s, which is adequate time for the film to be well mixed. Comparative experimental data were obtained in which an additional waiting period of 30 s was added after sampling and before the capillary was raised to the sampling position. Statistically, there was no difference, either in the absolute value of the signals or in the relative standard deviations.

The effect of the sampling period was also investigated. The sampling period effect was determined for dry $SO_2$ gas at two different concentrations (18 ppbv and 34 ppbv) at six different nominal sampling periods ranging from 13 s to 100 s at a constant sampling rate of 100 cm$^3$/min. The responses may be described by the following linear equations:

$$\text{peak } ht = 0.294 \pm 0.020 \text{ (sampling time)} + 4.25 \pm 1.36 \quad (4)$$

$$r = 0.9928$$

and $$\text{peak } ht = 0.528 \pm 0.008 \text{ (sampling time)} + 9.39 \pm 0.50 \quad (5)$$

$$r = 0.9995$$

These data show that the ratio of the slopes is in the ratio of the sampled concentrations, within experimental uncertainty. The finite positive intercepts are real, and result from the fact that the film spends some time in the sampling chamber before and after the nominal sampling period. No attempts were made in these experiments to flush out the chamber between experiments.

Thus, the sampling period was essentially extended beyond the nominal value, not accounted for in equations (4) and (5), above. This period can be calculated by dividing the intercept with the slope. Within experimental uncertainty, these values are identical for equations (4) and (5), 16±2 s. If this time is included in the sampling period, equations (4) and (5) can be expressed in terms of a zero intercept.

Another factor, not accounted for above, also plays a role in such experiments. Evaporation of the film takes place during sampling (especially with a dry, approximately 10% relative humidity sample), although the volume injected remains the same. However, since it is reasonable to expect evaporative loss to be linearly dependent upon time, this factor is incorporated in the linear relationship observed. As described later herein, evaporation loss can be compensated for using an internal standard, although this is not essential to understand the dependence of the signal on the sampling period. Evaporative loss, however, sets an upper limit on the permissible sampling period. Dry sample gas naturally sets the most stringent limit. According to the present invention in which a loop/film is used, this limit is 120 s at a sampling rate of 100 cm$^3$/min.

Figure 6:
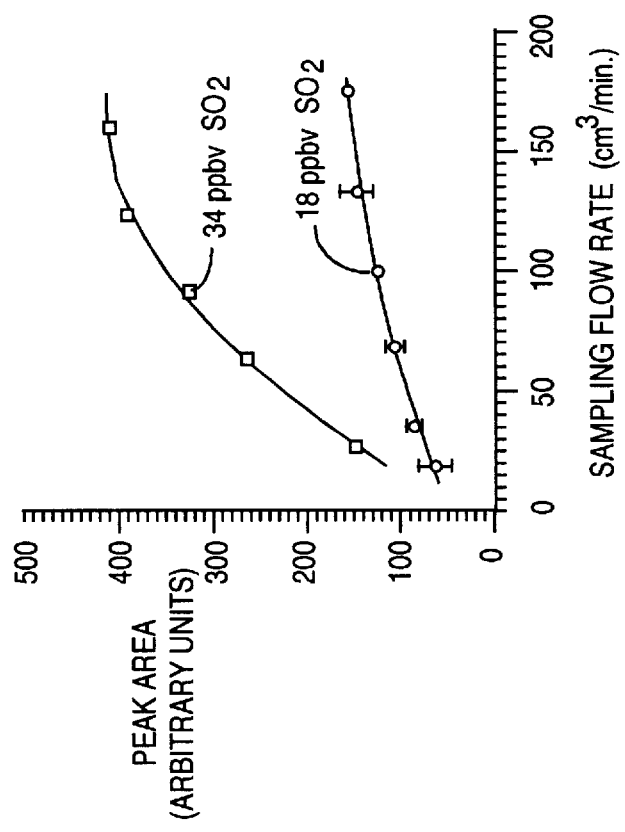
FIG. 6 depicts sampling flow rate versus peak area as a function of concentration, according to the present invention.

The effects of sampling flow rate and collection efficiency were also investigated. FIG. 6 shows signal dependence on sampling flow rate in the range of 16 cm$^3$/min to 175 cm$^3$/min for a fixed sampling time of 40 s for $SO_2$ concentrations of 18 ppbv and 34 ppbv. Error bars on the 18 ppbv lower curve data represent standard deviations (n=3). As shown in FIG. 6, the pattern displays an initially steep dependence upon flow rate, with a continued decrease in flow rate dependence with increasing flow rate. The pattern eventually culminates to a situation where there is essentially no flow rate dependence. Such patterns are quite typical of diffusion-based collection in the laminar flow regime. One particularly advantageous aspect of such dependence on sampling rate is that one can operate in the higher flow rate regime. In such regime, the effect of the flow rate is minimal, and expensive measures for flow control are not needed.

The fraction of the sample gas that is actually collected by the film decreases with increasing sample rate. The mass of $SO_2$ introduced into the sampling chamber is known. One can compare the signal obtained therefrom with the signal resulting from an aqueous sulfate standard introduced from the loop. Using such comparison, one finds that under a typical experimental condition (45 mM $H_2O_2$, 100 cm$^3$/min sample for 60 s, 20 ppb $SO_2$), about 10% of the analyte gas is collected by the film. Since this value is far from quantitative, control should be impressed upon the parameters that affect the collection efficiency. The most notable such parameter is temperature, which affects the diffusion coefficient of the sample gas. Since the flow rates and the size of the sampling system are small on an absolute scale, thermal mass is low. Thus the task of thermostating should be simple.

Figure 7:
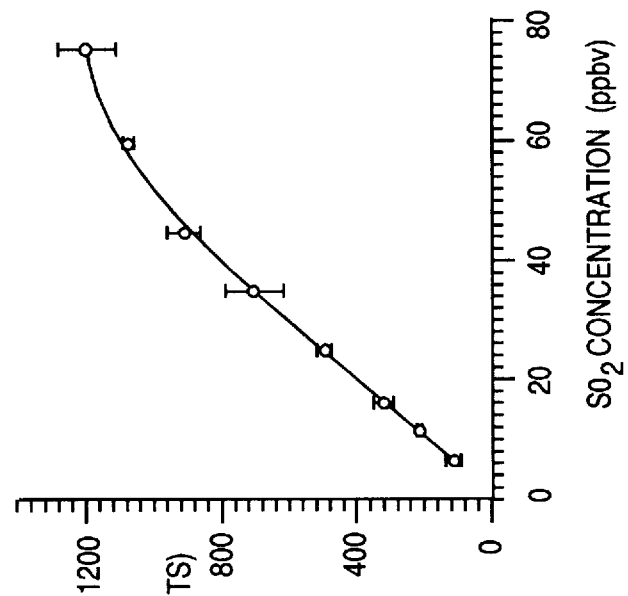
FIG. 7 depicts a calibration curve showing peak area versus concentration, according to the present invention.

FIG. 7 shows a calibration plot for 6 ppbv to 80 ppbv $SO_2$, using 45 mM $H_2O_2$ as the absorber, with a 100 cm$^3$/min flow rate and 60 s sampling time. The response is linear up to about 50 ppbv under these conditions, but clearly shows decreased response at higher concentrations. However, for the majority of ambient applications, this range and degree of linearity is adequate.

The $H_2O_2$ concentration clearly plays a role in determining the applicable linear range. In the range of 0 ppv to 50 ppb $SO_2$, the linear r$^2$ value for the concentration versus peak area relationship increases from 0.9868 to 0.9962 as the $H_2O_2$ concentration is increased from to 8.8 mM to 35 mM.

However, $H_2O_2$ concentration is not the only factor in maintaining constant collection efficiency as the sample concentration is varied. Since $H_2SO_4$ is formed on the surface of the film and is slow to diffuse into the interior, surface accumulation of acidity results in impaired uptake of $SO_2$. It is interesting to note in this context that the electropherogram shows both a sulfite and a sulfate peak only when the concentrations of sampled $SO_2$ and the $H_2O_2$ absorber are both low. Otherwise, sufficient $H_2SO_4$ is formed to preclude the significant presence of sulfite. In the current age of data processing technology, an excessive emphasis of the linearity of calibration may be is not fruitful. As long as sufficient slope is present, the analytical parameter of interest can be computed with equal ease from a nonlinear calibration plot stored in computer memory.

The above behavior is likely unique for the particular gas-absorber combination when a weak acid gas reacts to form a strong acid on the surface. In any case, the upper range of linearity can readily be manipulated by controlling the total amount of analyte collected. This may easily be done by changing the sampling time.

The effect of relative humidity was investigated. The above-described experiments were conducted under dry conditions. During sampling, solvent in the film evaporates, the loss increasing with the sampling rate, sampling period, and decreased sample relative humidity. Evaporation thus results in concentration of the analyte in the film. Water vapor may normally have intrinsic effects such as forming water clusters in the gas phase with the analyte, thus decreasing the diffusion coefficient and decreasing collection efficiency of the analyte.

However, regardless of any water vapor intrinsic effect, decreased sample relative humidity will result in a greater concentration of the analyte injected, for the same total analyte mass collected by the film. This concentration effect can be substantial, in that a best fit linear calibration slope decreases by 45% as the sample relative humidity increases from 10% to 80%. But this concentration effect can be largely compensated for if a stable internal standard, one not likely to occur in the sample gas, is incorporated in the film forming liquid at a constant concentration.

For compensation purposes, 1 mg/L chlorate was selected. From 10% to 57% relative humidity, the calibration slope decreased by 31%. But with internal standard correction, the difference decreased to less than 12%. Use of an internal standard may also otherwise improve precision.

The residual effect of the influence of relative humidity is real, however. Applicant has not generally encountered a relative humidity dependence for $SO_2$ in other diffusion based collection systems. The effect observed is not insubstantial in that the calibration slope decreases by 35% from 10% to 80% relative humidity, even after internal standard correction. The overall flow in the test system is low, and applicant believes that what is encountered may be actual losses of $SO_2$ from the test stream because of adsorption of water vapor on the wall. Due to the low flow rates involved, the system never reaches adsorption equilibrium.

Because of the high sensitivity of the preferred system, it may be practical to dilute the sample gas with highly humid air to keep the relative humidity high. Interestingly, at 80% relative humidity, sampling readily can be conducted for more than 10 minutes. Evaporation is sufficiently low such that the film remains intact for a very long period of time. By thus increasing the sampling time it may actually be possible to improve on the concentration limit of detection, even though the sample is pre-diluted.

Overall reproducibility of gas sampling on a liquid film and measurement by an aliquot injection therefrom, according to the present invention, was investigated. Precision data were reported as percent relative standard deviation ("RSD") for peak area, percent relative standard deviation for peak height, ppbv $SO_2$ sampled, n=3 at each concentration level). The precision data were 14.3, 8.3, 6.7 ppb; 3.1, 4.9, 11.6 ppb; 8.8, 4.0, 16.4 ppb; 4.3, 10.8, 25.7 ppb; 12.1, 8.S, 35.9 ppb; 5.7, 3.0, 45.5 ppb; 1.5, 5.6, 60.8 ppb and 7.4, 5.5, and 77 ppb.

Considering the low parts per billion ("ppb") levels of these measurements and the attendant sources of error in the generation/transmission of the calibrant gas, dilution gas purity and blank variability, these results are quite acceptable. Thus, aliquot sampling from the film, according to the present invention, is an acceptable process for sample introduction from the film.

The limit of detection for $SO_2$ is clearly dependent on a number of variables, including sampling rate and sampling duration. FIG. 8A is an electropherogram resulting from 1.5 ppbv $SO_2$ sampled for 1 minute at 100 cm$^3$/min, and FIG. 8B is a similar electropherogram for 2 minute sampling. Longer sampling periods are obviously possible if the sample air is not completely dry. In any case, a level of detection of about 1 ppbv can be conservatively estimated for any sample relative humidity.

Electromigration is often practiced to improve levels of detection, but is not readily practiced with a SUCCESS-type system such as shown in FIG. 2 because electroendosmotic flow ("EOF") dominates electrophoretic movement, and the two effects oppose each other. However, if an indirect optical detection approach is used with a cationic surfactant as a flow modifier, if and negative high voltage potential is used for operation, it is in fact straightforward and reproducible to practice electromigration by using the loop wire 200 itself as the high voltage electrode. This approach is especially valuable if such detection methods, as opposed to suppressed capillary electrophoresis, is used for detection.

Figure 9B:
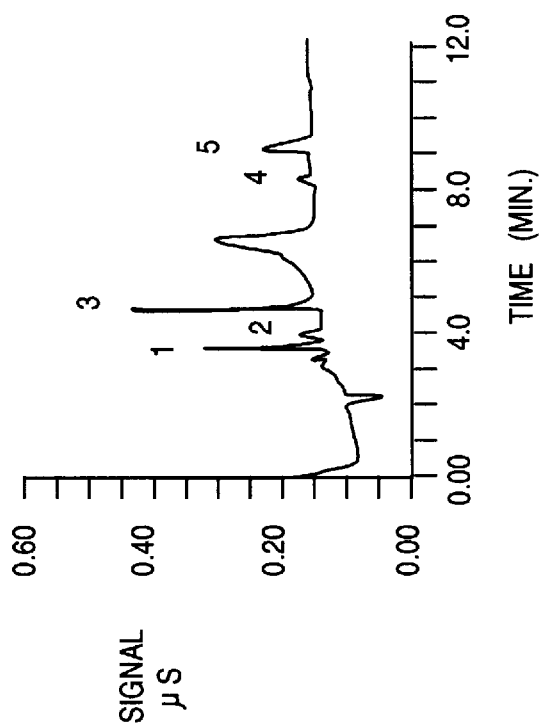
FIGS. 9A–9D are electropherograms of various gases, according to the present invention.
Figure 9A:
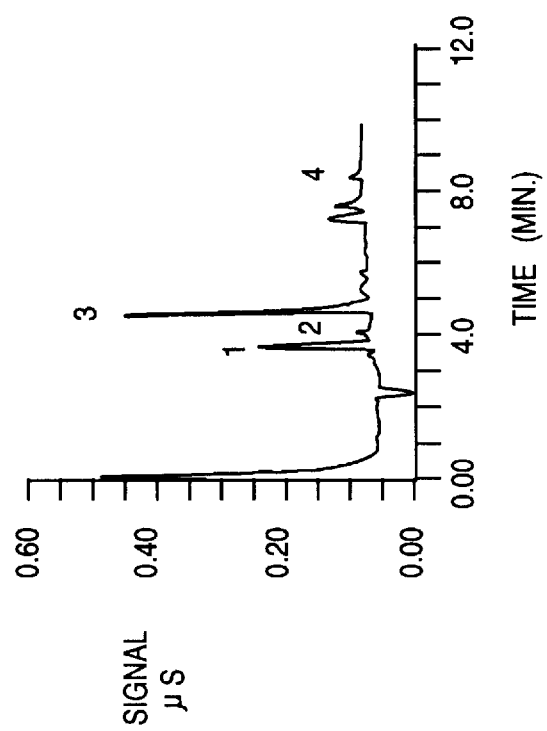
Figure 9D:
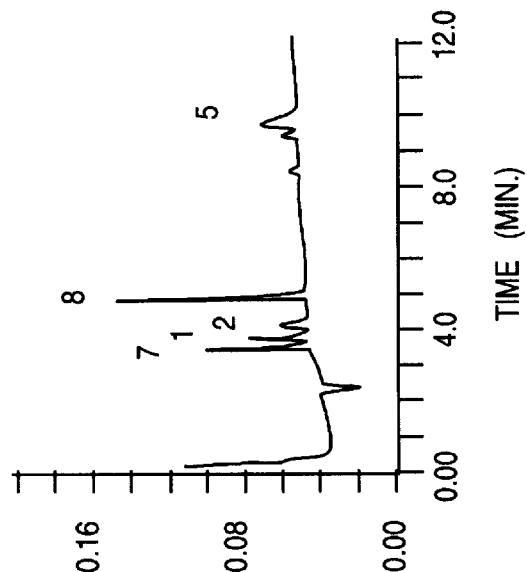
Figure 9C:
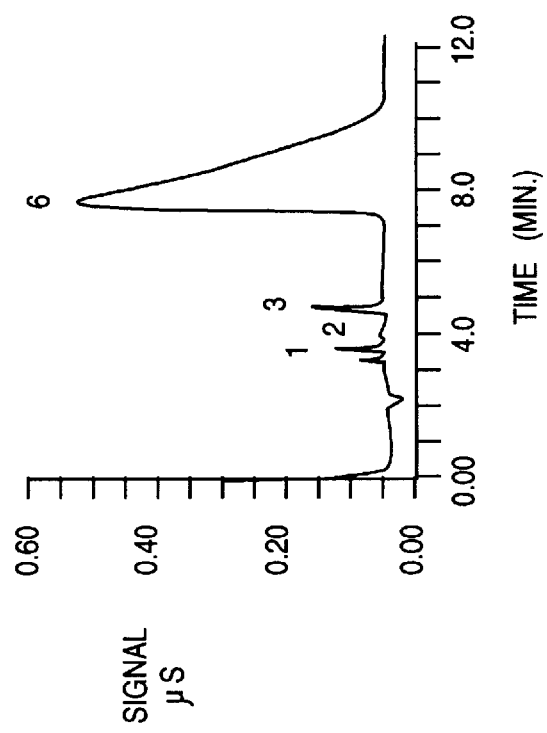

It will be appreciated that present invention can readily be used in a variety of applications, examples of which are depicted in FIGS. 9A–9D. FIG. 9A is an electropherogram of detection signal versus time, showing the significant occurrence of formic and acetic acids in the air outside the Texas Tech University chemistry building. FIG. 9B reflects data for vapors taken over a freshly cut onion. In FIG. 9C, volatile impurities in vapors taken from a bottle of concentrated $HClO_4$ (15 s sampling time) are shown. Finally, FIG. 9C a $CO_2$ peak is observed in vapors collected over a half empty can of carbonated beverage, from which most of the carbonation had dissipated. In FIGS. 9A–9D, the following migration-based identifications are shown: 1=acetate, 2=carbonate, 3=formate, 4=nitrate, 5=sulfate (probably originally sulfite), 6=perchlorate and chloride overlapped (but resolvable at lower concentrations), 7=benzoate, and 8=phosphate. Peaks unlabelled in these electropherograms could not be readily identified.

Applicant believes the present invention represents the first example of direct determination of gases by capillary electrophoresis. The simple technique reported here can vastly expand capillary electrophoresis (possibly the most powerful and elegant separation technique of the decade) to gaseous analyses. It is likely that future applications of the present invention for organic vapors, using micellar electrokinetic chromatography or nonaqueous electrophoretic media can be expanded beyond what has been described herein. Applicant's method of sampling from a film formed on a loop may, for example, find use in electromigrative injections from the loop, and indeed the loop may be used as a sample extraction interface in other biphasic systems.

In summary, according to the present invention a liquid droplet or a film is used to provide a gas sampling interface that advantageously is indefinitely renewable and may be deployed in a microscale. Further, due to evaporative flux from the droplet/film, the approach of particles is greatly inhibited.

Modifications and variations may be made to the disclosed embodiments without departing from the subject and spirit of the invention as defined by the following claims on a microscale.

What is claimed is:

1. A method for introducing an analyte in a solution into the input end of a separation capillary in a capillary separation system for electric-field separation of said analyte from another substance in said solution, the method comprising the following sequential steps:

(a) providing a microreservoir by forming a loop having a transverse dimension and defining a plane substantially parallel to a longitudinal axis of said separation capillary, said loop being formed adjacent said input end of said separation capillary; and (b) contacting said loop with said solution to form a sample of said solution containing said analyte as a film across an area defined by said loop such that at least a portion of said sample is in fluid communication with said input end of said separation capillary.

2. The method of claim 1, wherein step (a) further includes forming said loop in a manner selected from a group consisting of (i) forming said loop having said transverse dimension of about 2 mm, (ii) forming said loop from wire, and (iii) forming said loop from wire and attaching said loop to said input end of said separation capillary by wrapping a length of said wire around said input end.

3. The method of claim 1, further including a subsequent step (c) of injecting at least a portion of said sample into said separation capillary using electromigration.

4. The method of claim 1, further including a subsequent step (c) of pneumatically applying pressure to urge at least a portion of said sample into fluid communication with said input end of said separation capillary.

5. The method of claim 1, further including a subsequent step (c) of elevating said loop relative to said input end of said separation capillary such that gravity promotes fluid communication therebetween.

6. The method of claim 1, further including:
   a subsequent step (c) of urging at least a portion of said sample into fluid communication with said input end of said separation capillary; and
   a subsequent step (d) of electrophoretically separating said analyte from another substance present in said solution;
   wherein during step (d) said loop forms one electrophoretic electrode.

7. For use with a capillary separation system in which an analyte in a medium is to be separated from another substance in said medium for measurement, a capillary-microreservoir sampling unit, comprising:
   a separation capillary having an input end into which said analyte in said solution is to be introduced; and
   a microreservoir comprising a loop having a transverse dimension and defining a plane substantially parallel to a longitudinal axis of said separation capillary adjacent said input end, said loop being disposed adjacent said input end of said separation capillary;
   said loop defining an area across which a sample comprising a film of liquid may be formed by contacting said liquid with said loop.

8. The capillary-microreservoir sampling unit of claim 7, wherein said loop has a characteristic selected from a group consisting of (i) said loop has a transverse dimension of about 2 mm, (ii) said loop is formed from wire, (iii) said loop is formed from platinum wire, and said loop is formed from wire and is attached to said input end of said separation capillary by a length of said wire wrapped around said input end.

9. A method for introducing an analyte in a gas into the input end of a separation capillary in a capillary separation system for electric-field separation from another substance in the gas, the method comprising the following sequential steps:
   (a) providing a microreservoir by forming a loop having a transverse dimension and defining a plane substantially parallel to a longitudinal axis of said separation capillary, said loop being formed adjacent said input end of said separation capillary; and
   (b) contacting said loop with a liquid able to absorb at least a portion of said analyte such that a film containing said liquid is formed across an area defined by said loop; and (c) exposing said loop to said gas such that at least a sample comprising a portion of said analyte is absorbed in said film such that at least a portion of said analyte in said film is in fluid communication with said input end of said separation capillary.

10. The method of claim 9, wherein step (a) includes forming said loop in a procedure selected from a group consisting of (i) forming said loop with said transverse dimension of about 2 mm, (ii) forming said loop from wire, and (iii) forming said loop from wire and attaching said loop to said input end of said separation capillary by wrapping a length of said wire around said input end.

11. The method of claim 9, further including a subsequent step (d) of electrophoretically separating said analyte;
    wherein during step (d) said loop forms one electrophoretic electrode.

12. The method of claim 9, further including a subsequent step (d) of pneumatically applying pressure to urge at least a portion of said sample into fluid communication with said input end of said separation capillary.

13. The method of claim 9, further including a subsequent step (d) of elevating said loop relative to said input end of said separation capillary such that gravity promotes fluid communication therebetween.

14. A method for introducing an analyte in a first solution into the input end of a separation capillary in a capillary separation system, the method comprising the following sequential steps:
    (a) providing a microreservoir by forming a loop having a transverse dimension and defining a plane substantially parallel to a longitudinal axis of said separation capillary, said loop being formed adjacent said input end of said separation capillary; and
    (b) contacting said loop with a second solution that is immiscible to said first solution such that a film of said second solution is formed across an area defined by said loop; and
    (c) exposing said loop to said first solution such that at least a sample portion of said analyte in said first solution is carried by said second solution in said film through a biphasic interface thereon, wherein at least a portion of said analyte in said film is in fluid communication with said input end of said separation capillary.

15. The method of claim 14, wherein step (a) includes forming said loop in a procedure selected from a group consisting of (i) forming said loop with said transverse dimension of about 2 mm, (ii) forming said loop from wire, and (iii) forming said loop from wire and attaching said loop to said input end of said separation capillary by wrapping a length of said wire around said input end.

16. The method of claim 14, further including a subsequent step (d) of injecting at least a portion of said sample into said separation capillary using electromigration.

* * * * *